US00PP25066P3

(12) United States Plant Patent
Zeldin et al.

(10) Patent No.: US PP25,066 P3
(45) Date of Patent: Nov. 18, 2014

(54) CRANBERRY PLANT NAMED 'WI92-A-X15'

(50) Latin Name: ***Vaccinium macrocarpon* Ait.**
Varietal Denomination: WI92-A-X15

(75) Inventors: Eric Zeldin, Madison, WI (US); Brent McCown, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 115 days.

(21) Appl. No.: 12/804,830

(22) Filed: Jul. 29, 2010

(65) Prior Publication Data

US 2012/0030847 P1 Feb. 2, 2012

(51) Int. Cl.
*A01H 5/00* (2006.01)
*A01H 5/08* (2006.01)

(52) U.S. Cl.
CPC ..... *A01H 5/08* (2013.01)
USPC ..... Plt./156

(58) Field of Classification Search
USPC ..... Plt./156
See application file for complete search history.

(56) References Cited

U.S. PATENT DOCUMENTS

| | | | |
|---|---|---|---|
| PP14,225 | P2 | 10/2003 | McCown et al. |
| PP18,252 | P3 | 11/2007 | Vorsa |
| PP18,911 | P2 | 6/2008 | Vorsa |
| PP19,434 | P3 | 11/2008 | Vorsa |

OTHER PUBLICATIONS http://www.ino.ca/en/examples/anthocyanin-content-detection-system-%28tacy%29/, Anthocyanin Detection System (TACY), INO, pp. 1-4, 2014.*
Bubel et al., Digital TAcy: proof of concept, vol. 7386, Abstract, 2009.*
McCowen et al., "Future cranberry selections: which trait is critical for 2050," 2010 Wisconsin Cranberry School, Jan. 12-13, 2010, Stevens Point, WI. (Abstract).
Roper, "'Stevens' cranberry," *Journal of the American Pomological Society,* 55(2), pp. 66 and 67, 2001.

* cited by examiner

*Primary Examiner* — Kent L Bell
(74) *Attorney, Agent, or Firm* — Dentons US LLP

(57) ABSTRACT

A new and distinct cranberry variety 'WI92-A-X15' is described. The variety is distinguished by significantly higher yields, larger fruit size, more favorable bud set traits, tolerance to high levels of fertilizer, higher and earlier red pigmentation, and ability to set excellent crops at an early age as compared to 'Stevens', the most widely grown cranberry cultivar. 'WI92-A-X15' was derived from a controlled cross of the variety 'Stevens' and an open-pollinated seedling selection of the variety 'Ben Lear' designated as Boone's 'BL8'.

4 Drawing Sheets

Latin name of the genus and species of the plant claimed: *Vaccinium macrocarpon* Ait.

Variety denomination: 'WI92-A-X15'.

BACKGROUND OF THE INVENTION

The present invention relates to a new and distinctive cranberry variety having significantly higher yields, larger fruit size, more favorable bud set traits, tolerance to high levels of fertilizer, high red pigmentation and ability to produce excellent crops at an early age as compared to the leading commercial cultivar, 'Stevens'.

The American cranberry, *Vaccinium macrocarpon* Ait., is a small fruit grown commercially in the temperate regions of North America and Chile. The United States is presently the major producer of cranberries, with the combined Wisconsin and Massachusetts harvests accounting for the majority of U.S. and world annual production. Currently Wisconsin produces over half of the U.S. crop.

The American cranberry is well known for its tart flavor and its red pigment. The importance of adequate pigment content (measured as total anthocyanins or Tacy, and expressed as mg per 100 grams fresh fruit) is recognized by most processors as they are known to give a reduced value to poorly colored fruit. Cranberry selections widely grown today have generally not experienced the extensive breeding as seen in other fruit-bearing species. Many selections were derived directly from native areas or from managed beds of mixed origin. For example, 'Ben Lear' (unpatented) is a cranberry selection taken directly from the wild in Wisconsin in the early 1880's, and is widely grown in short-seasonal areas due to its early fruit development and high color content. The U.S. Department of Agriculture undertook, in cooperation with state experimental stations, one generation of breeding in an attempt to improve U.S. cranberry cultivars. The breeding resulted in the introduction of the 'Stevens' (unpatented) variety in 1950. The 'Stevens' variety is today the most widely grown cultivar and is characterized by dependably good yields, but only moderate color development, especially in short-seasonal regions such as Wisconsin.

BRIEF SUMMARY OF THE INVENTION

The present invention relates to a new and distinct cranberry variety. The variety is designated 'WI92-A-X15' and was produced through controlled breeding performed in 1990 in Dane County, Wis. Cranberry variety 'WI92-A-X15' is derived from a controlled cross of the 'Stevens' variety as the female parent and a selection designated Boone's 'BL8'

(originally derived from an open-pollinated population of seedlings of 'Ben Lear') as the male parent.

'WI92-A-X15' cranberry was initially selected based on large berry size in August of 1992 and was propagated for field trials planted in 1994. 'WI92-A-X15' was initially asexually propagated from a single stem via micropropagation (surface sterilization, followed by continuous shoot culture, without plant growth hormones, on Woody Plant Medium) in Madison, Wis. 'WI92-A-X15' demonstrated continued production of large berries and favorable bud set traits, including both good fruit bud set in general and excellent bud set on fruiting stems ('uprights') specifically. 'WI92-A-X15' was compared to 'Stevens' both in plots within common beds (2004 and 2009 data presented in FIG. 2-4) and in full beds utilizing a 0.66 acre dedicated bed planted in 2006 and on a 2 acre portion of a larger bed planted in 2007. In late September of 2009, four years after planting, the 0.66 acre bed was harvested and in mid-October of 2009, three years after planting, the 2 acre bed was harvested. The yields were compared to established beds of 'Stevens' harvested in the same time period (Table 1).

'WI92-A-X15' exhibits significantly higher yields (up to approximately two times higher than variety 'Stevens'), larger fruit size, more favorable bud set traits, tolerance to high levels of fertilizer, earlier and higher red pigmentation, and an ability to set excellent crops at an early age as compared to 'Stevens'.

'WI92-A-X15' has been compared to 'Stevens', one of its parental varieties and the cultivar that it will replace. Boone's 'BL8' is not a cultivar and has not been grown side by side with 'WI92-A-X15'. Boone's 'BL8' shares some traits with 'WI92-A-X15', but can be readily distinguished by its limited stolon production, limited number of flowering stems per unit area (and thus reduced yield), and a higher pigment content (both timing and initial accumulation). The above are observational, but reproducible and confirmed by grower/cooperators. 'WI92-A-X15' has been grown side by side with 'Ben Lear', the parent of Boone's 'BL8', and data and photographic evidence is available that shows a larger average fruit size and a markedly different fruit size distribution when expressed as percent of yield in a certain size class (e.g., 60% of yield in berries 2 g and above for 'WI92-A-X15', 13% for 'Ben Lear').

DETAILED BOTANICAL DESCRIPTION

Figure 1:
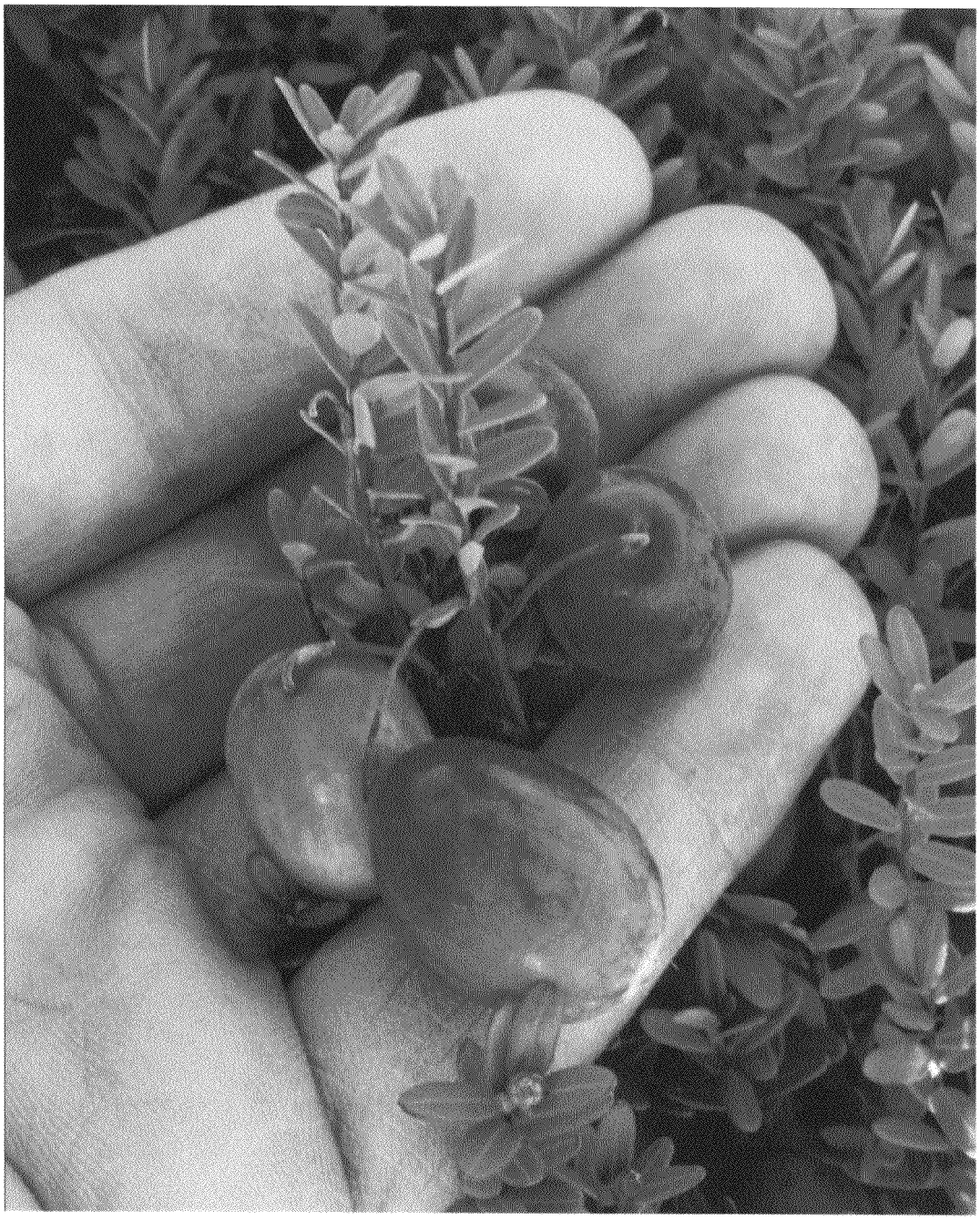
FIG. 1. 'WI92-A-X15' uprights with fruit, Monroe County, Wis., Sep. 30, 2009. Note the large size and good pigmentation of the fruit and the presence of flower buds on the fruiting upright tips.

The distinctive characteristics of the new 'WI92-A-X15' variety are shown in Tables 1 and 2 and described in detail below.

Visual analysis of 'WI92-A-X15' cranberry samples taken between early September and early October 2009 demonstrated fruit color development and fruit size exceeding that of parent cultivar 'Stevens'. 'WI92-A-X15' fruit from the four-year-old, 0.66 acre bed and the three-year-old, 2 acre bed were harvested at the beginning of October and mid-October of 2009, respectively, and comparison 'Stevens' fruit was harvested over the course of several weeks in October. Yields from each 'WI92-A-X15' bed were compared to established beds of 'Stevens' over the whole farm and specific beds indicated in Table 1 (see Table 1 for harvest dates). Yield is expressed as barrels per acre or B/a, 1 barrel=100 lbs. As shown in Table 1, cranberries from the four-year-old 'WI92-A-X15' bed out-performed the established variety 'Stevens' by about two-fold, yielding 476 B/a versus a farm average of 243 B/a for 66 acres of 'Stevens'. Examples of individual beds of 'Stevens' show a range from 217 to 278 B/a. The three-year-old 'WI92-A-X15' had a yield similar to that of established 'Stevens' with 242 B/a. In contrast, the yields produced from two beds of 'Stevens' planted in 1995, produced 153 and 156 B/a as three-year-olds, respectively, and 192 and 204 B/a as four-year-olds, respectively.

'WI92-A-X15' was not only able to produce higher yields, but the fruit color was favorable when compared with 'Stevens'. The 0.66 acre bed of 'WI92-A-X15' was harvested eight to fifteen days earlier than the 'Stevens' beds, yet had nearly equivalent fruit color (Table 1). The 2 acre area of 'WI92-A-X15' was harvested only a few days later than the 'Stevens' beds, yet had fruit color approximately 50% greater.

TABLE 1

Yield comparison of 'WI92-A-X15' and 'Stevens' cranberry varieties in 2009 at a commercial cranberry farm in Wood County, Wisconsin.

| | 'WI92-A-X15' | | 'Stevens' | | |
|---|---|---|---|---|---|
| | | | | Specific 'Stevens' beds (all at least 10-yr-old) | |
| | 4-yr-old | 3-yr-old | Overall | A14 | A18 |
| Yield (B/a) | 476 | 242 | 243 | 217 | 236 |
| Size (acres) | 0.66 | 2.00 | 66 | 3.17 | 4.59 |
| N applied (lbs/acre) | 74 | 74 | 42 | 42 | 42 |
| Harvest date | Oct. 1 | Oct. 17 | — | Oct. 10 | Oct. 9 |
| Tacy (mg/100 g) | 26 | 47 | — | 29 | 27 |

| | 'Stevens' Specific 'Stevens' beds (all at least 10-yr-old) | | |
|---|---|---|---|
| | A6 | A20 | A24 |
| Yield (B/a) | 278 | 248 | 229 |
| Size (acres) | 2.27 | 4.06 | 3.58 |
| N applied (lbs/acre) | 42 | 42 | 42 |
| Harvest date | Oct. 15 | Oct. 12 | Oct. 9 |
| Tacy (mg/100 g) | 30 | 28 | 27 |

High rates of nitrogen can cause excessive vegetative growth, or "overgrowth", resulting in numerous non-fruiting stolons growing over the top of the canopy. 'Stevens' is particularly susceptible to such nitrogen induced overgrowth, which can be associated with reduced yields. Unlike 'Stevens', 'WI92-A-X15' displays little overgrowth, no reduced yields, and no changes in berry size or upright average growth when treated with high levels of nitrogen; instead 'WI92-A-X15' displays an increase in flower bud set under high nitrogen fertilization. The tolerance of cranberry variety 'WI92-A-X15' to high levels of fertilizer can be seen in Table 2. The effects of increased fertilizer and the tolerance thereto displayed by 'WI92-A-X15' is also demonstrated in Table 1 as the yields shown for 'WI92-A-X15' were not adversely affected by the significantly higher units of nitrogen applied than what was used for 'Stevens'.

In early October of 2009 the tolerance of 'WI92-A-X15' to increased nitrogen was evaluated at a testing site near Tomah, Wis. Plots of 'WI92-A-X15' were fertilized with nitrogen levels used throughout the bed or received additional fertilizer from three extra applications of ammonium sulfate as well as a slow release fertilizer. Table 2 shows the resulting effects of nitrogen treatment of five samples of 'WI92-A-X15'. In particular, the high nitrogen treated plot of 'WI92-A-X15' did not display overgrowth, reduced yields or differences in berry size or upright average growth; instead a slight increase in yield and a large increase in flower bud set was observed.

TABLE 2

Effects of low and high nitrogen (N) fertilization on yield and other characteristics in 'W192-A-X15' cranberry variety in 2009 near Tomah, WI. (numbers in parentheses denote standard error)

| Treat-ment | Units N (lbs/acre) | Yield (B/a) | Avg. berry weight (g) | Avg. upright fresh wt.(g) | Flower bud set (%) | Shoot N content (%DW) |
|---|---|---|---|---|---|---|
| Low N | 32 | 559 (36) | 1.65 (0.05) | 0.11 (0.01) | 28.5 (5.7) | 0.87 (0.04) |
| High N | 66+ | 612 (27) | 1.64 (0.03) | 0.10 (0.01) | 57.8 (8.0) | 1.16 (0.08) |

Figure 2:
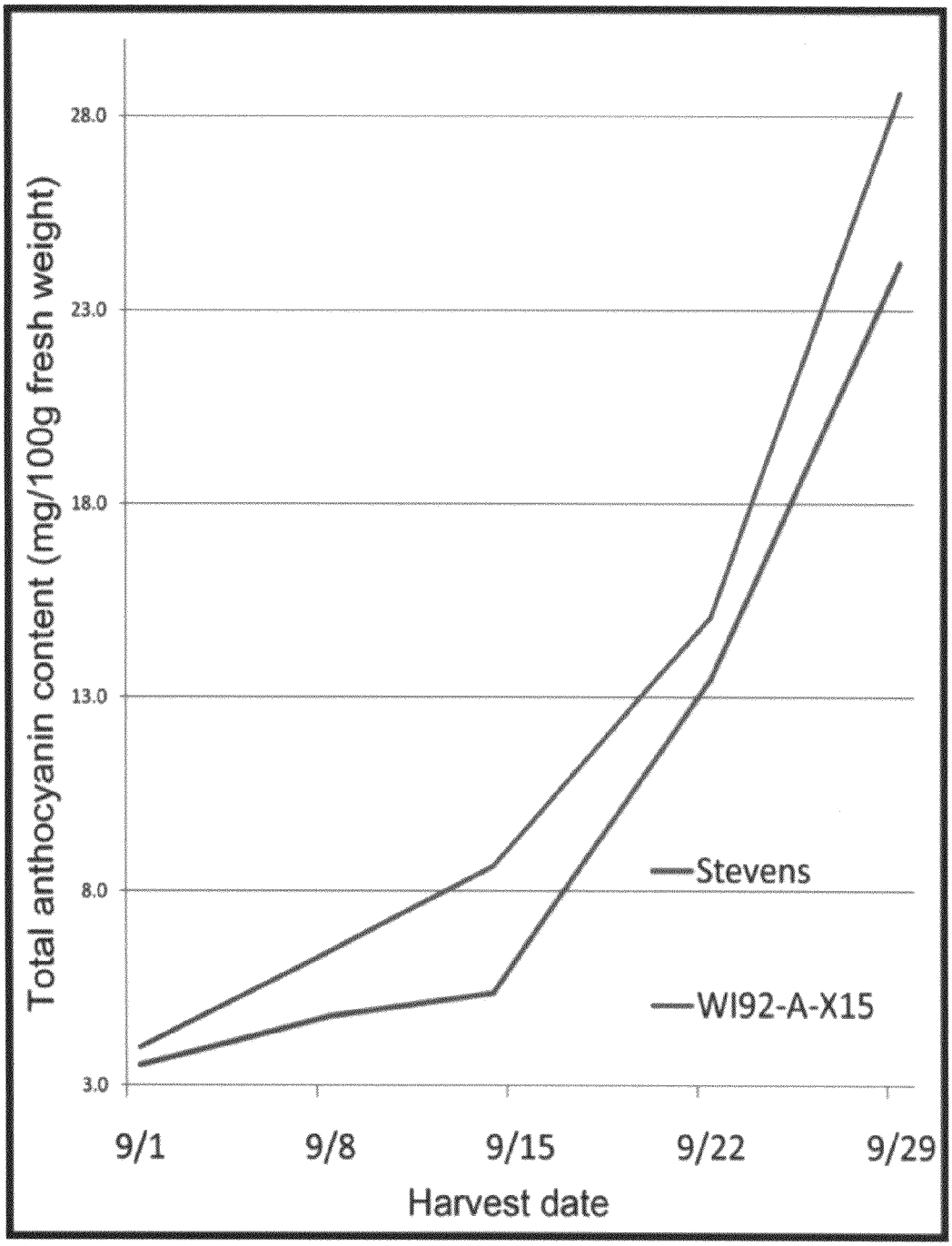
FIG. 2. Fruit color (anthocyanin) accumulation in fruit from plots of 'Stevens' and 'WI92-A-X15' during the late growing season of 2004 in a common bed in Wood County Wis. 'WI92-A-X15' pigmentation is consistently above 'Stevens'. Data presented is the average of six replicates for each time point for each variety.
Figure 3:
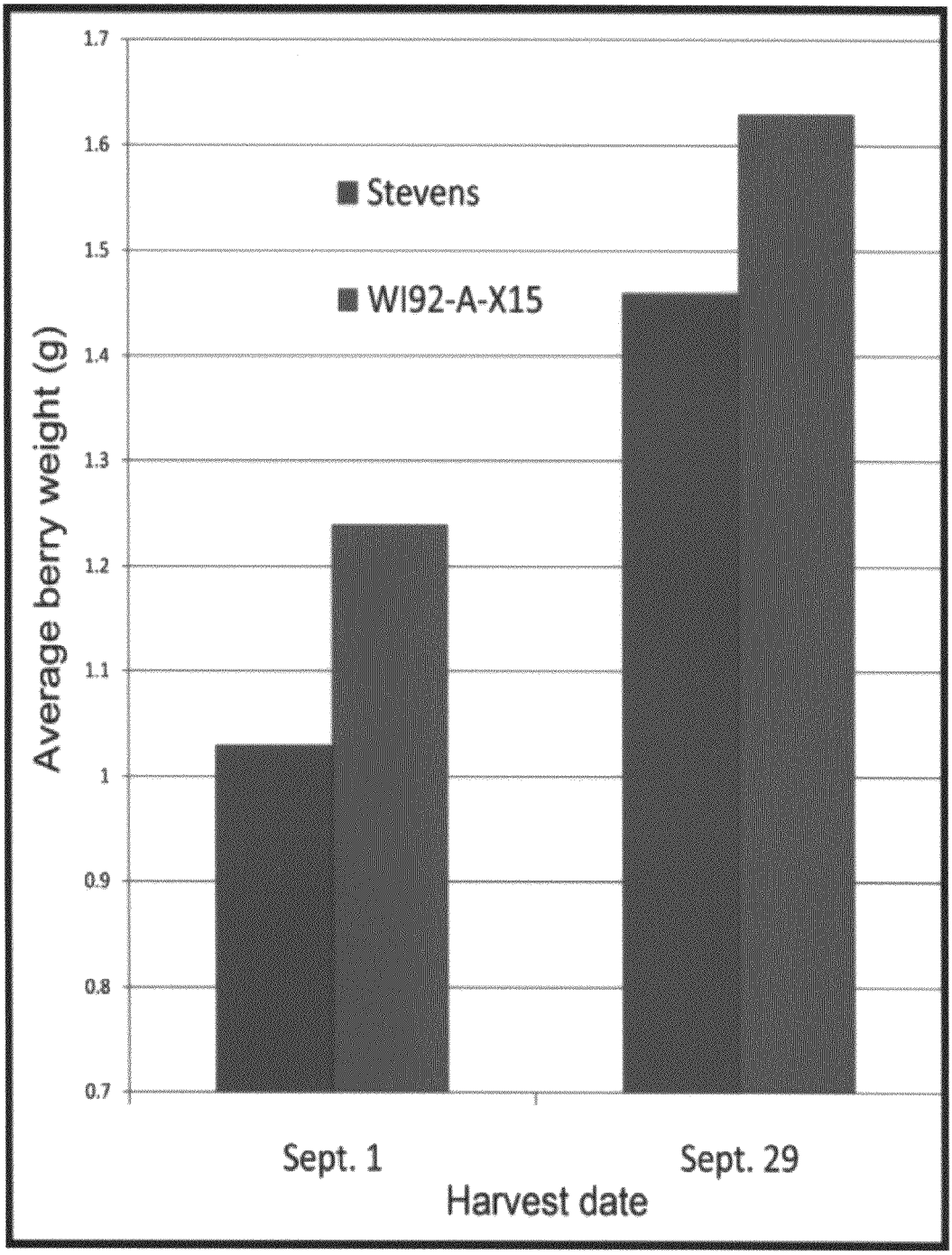
FIG. 3. Average berry size of fruit from plots of 'Stevens' and 'WI92-A-X15' at two points of the growing season of 2004 in a common bed in Wood County, Wis. (same plots as represented in FIG. 2). 'WI92-A-X15' displays both early and late berry bulking that leads to a larger berry size compared to 'Stevens'. Values are the average of six replicates for each harvest date for each variety.
Figure 4:
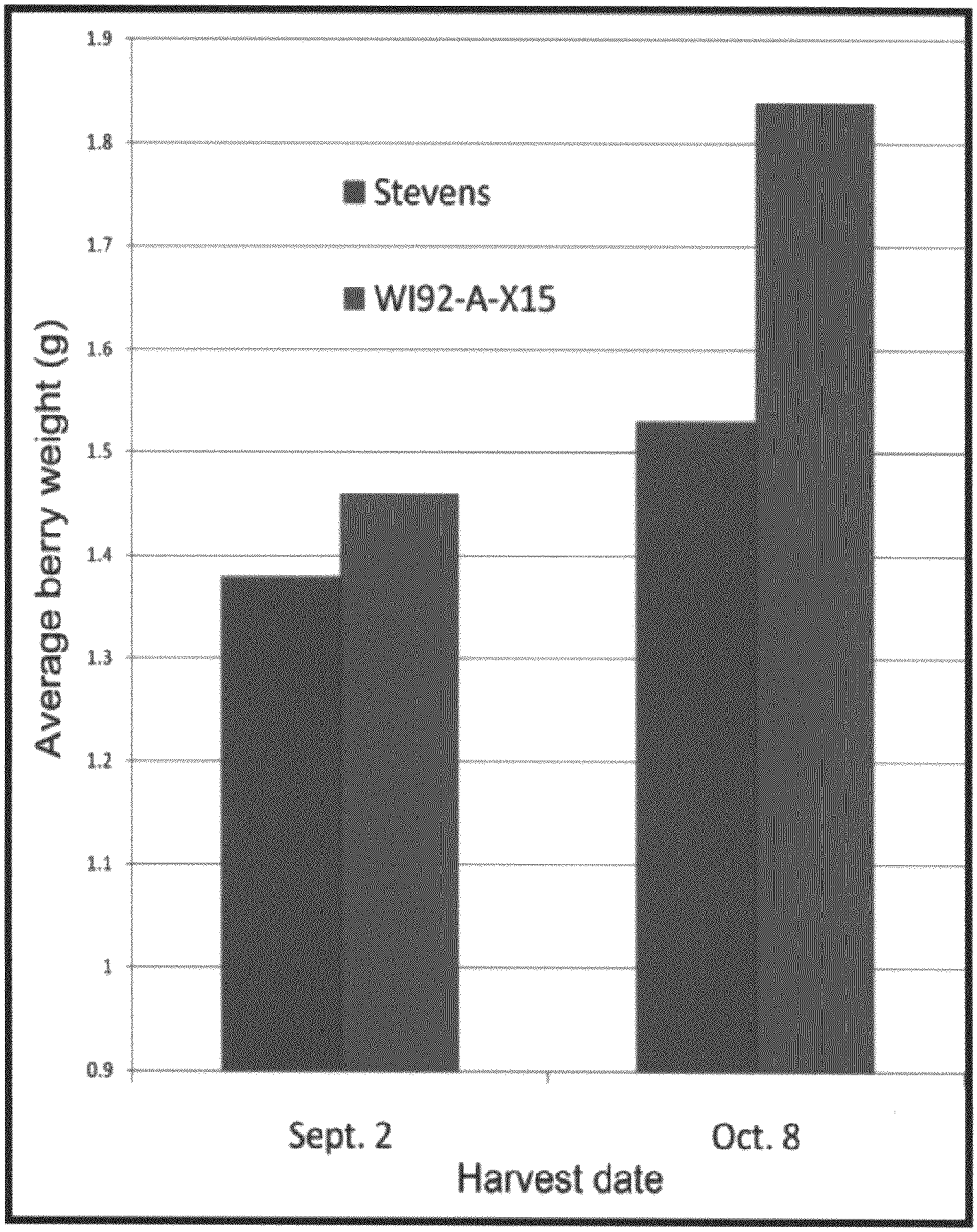
FIG. 4. Average berry size of fruit from plots of 'Stevens' and 'WI92-A-X15' at two points of the growing season of 2009 in a common bed in Wood County, Wis. (different location than that represented in FIG. 3). 'WI92-A-X15' uniformly has larger average berry size than 'Stevens', consistent with its original selection. Values are the average of three replicates for each harvest date for each variety.

The red pigment of cranberry is located almost entirely in the epidermal layers of the fruit. One factor which can to contribute to high extractable fruit color in cranberry is small fruit size, due in part to the influence of surface area to weight ratio on the total pigment content for each fruit. A negative correlation between yield and fruit color has also been suggested. However, 'WI92-A-X15' demonstrated better coloration in combination with increased fruit size and greater yield potential. Thus, 'WI92-A-X15' is able to produce high yields and large fruit size simultaneously with good fruit coloration (Table 1 and FIGS. 2-4.).

Thus, 'WI92-A-X15' is able to develop high levels of extractable pigmentation simultaneously with increased fruit size and yield.

The combination of the above 'WI92-A-X15' characteristics easily differentiates 'WI92-A-X15' from both its parents. The above characteristics also provide the 'WI92-A-X15' variety with benefits not recognized in other commercially grown and established varieties. For example, the increased yield and flower bud set of 'WI92-A-X15' provides the potential to increase both the current year's crop and the next year's crop through fertilizer regime. 'WI92-A-X15' additionally provides beneficial and distinct aspects over other cranberry cultivars as evidenced by its high yields. For instance, the observed approximately two times greater yield than the most planted 'Stevens' cultivar demonstrates a great advantage of the 'WI92-A-X15' variety.

Scientific name: *Vaccinium macrocarpon* Ait.

Parentage: The variety is a cross of the 'Stevens' variety and a selection designated Boone's 'BL8', which was derived from an open-pollinated population of seedlings of 'Ben Lear'.

Reproductive structures: The cranberry variety has both asexual (stolons) and sexual reproductive (fruit) structures.

Propagation: Cranberries can reproduce both asexually and sexually. For instance, stolons readily root when contacted with soil or reproduction may occur from seeds. Cranberry cultivars are propagated asexually through rooting of stolons and vertical shoots. Cranberry growers typically reproduce cranberries with either rooted or unrooted cuttings, or vine prunings that are broadcast and then pressed into the soil surface.

Productivity: 'WI92-A-X15' has out-yielded 'Stevens' by two-fold. In a four-year-old, 0.66 acre bed 'WI92-A-X15' yielded yielding 476 B/a while 'Stevens' produced a multi-bed farm average of 243 B/a. In a three-year-old, 2 acre bed 'WI92-A-X15' yielded 242 B/a, which was comparable to the yield observed for the established much older 'Stevens' beds, but yields were greater than from three and four-year old beds of 'Stevens' planted which produced an average of 154.5 B/a and 198 B/a, respectively. Yield data shown in Tables 1 and 2.

MORPHOLOGICAL DESCRIPTION OF CRANBERRY CULTIVAR 'WI92-A-X15'.

Growth habit: 'WI92-A-X15' produces fruit on upright stems, with vegetative expansion occurring by stolons. 'WI92-A-X15' can be distinguished by a very vigorous stolon growth in early plantings with sufficient fertilizer, but once older and heavily loaded with a crop, stolon growth is minimal (even under high fertilization). 'WI92-A-X15' can be differentiated from the industry standard cultivar, 'Stevens', by growth habit, in that when there is a significant crop load, it is less likely to form or elongate runners under high nitrogen fertilization. This is significant because it can lead to increased yield and increased flower bud set to increase yield the following year.

Runner length: During commercial establishment of new beds, high fertilization levels lead to primarily runner (stolon) growth, which ranges from three to six feet. Winter sand application and reduced fertilization leads to increased upright formation and eventually, upright stems, which are the desired reproductive tissue, become dominant and any runner formation is reduced. This true for all cranberry cultivars and selections.

Upright: Cranberry is not grown commercially as discrete plants, and thus evaluation of individual uprights per plant was not performed.

Leaves: All cranberry leaves are petiolate. Measurement of individual leaves was not performed.

Flowers: All cranberries produce flowers in the lower axils of new upright growth from pre-formed initials in flower buds. V. macrocarpon does not produce clusters, unlike some other *Vaccinium* species (notably *V. corybosum*, the commercial highbush blueberry). The flower number can vary greatly between flowering upright stems, both within a bed and between beds (due to age and management), and thus was not measured. Fragrance in cranberry is minimal.

Flower buds: Flower bud shape does not vary between cranberry cultivars, although the flower bud size can vary. Flower buds are small in all cranberry varieties, typically around 1 mm, variable, and all flower buds are round. Observationally, the flower bud size of 'WI92-A-X15' is similar to that of 'HyRed', typically a little larger than 'Stevens', and on average significantly larger than 'Ben Lear'. 'WI92-A-X15' has been observed to have a higher frequency of multiple buds per upright.

Flower petals: Cranberry in commercial production or even in the wild (with sufficient nutrient availability) does not vary much in flower size or other traits. 'WI92-A-X15' flower petals that are similar to the 'Stevens' parent and all other major cultivars. All cranberries have four petals, which are predominately white.

Sepals: Not measured.

Bloom time: Bloom time varies greatly with weather, season, and location, and occurs over several weeks. Bloom time is variable depending on the season but occurs from mid-June to early July. The relative time to mid-bloom (about 50% of flowers open) of 'WI92-A-X15' is similar to 'Stevens' and other major cultivars, which is about one week later than 'Ben Lear' and two weeks later than 'HyRed'.

Fruit: Fruit shape data can be useful in generally distinguishing cultivars, although these are highly variable within a planting bed, between beds, and based on location, age, and management method, among others. Table 1 provides total anthocyanin data, which is the accepted method within the cranberry industry to compare fruit between cranberry varieties. Yield and average berry weight for high and low nitrogen treatment is provided in Table 2. Other fruit characteristics are not useful in distinguishing cultivars and thus were not measured.

Fruit brix and titratable acidity: These characteristics vary very little between varieties compared to variation between growing regions, harvest date, season and location, and as such have little value in distinguishing cultivars. As such, these were not measured.

Harvest season: Harvest date is determined by growing region and also between individual growers and varies accordingly. However, a general description of harvest date for 'WI92-A-X15' would be between October $1^{st}$ and October $15^{th}$ in Central Wisconsin.

Winter hardiness: Commercial cranberries in Wisconsin are all winter protected by a thick layer of ice above the canopy.

Disease and pest resistance/susceptibility: No significant disease/pest resistance/susceptibility was observed in 'WI92-A-X15'.

What is claimed is:

1. A new and distinct variety of cranberry plant named 'WI92-A-X15' as herein described and illustrated.

* * * * *